US008592406B2

(12) United States Patent
Baek et al.

(10) Patent No.: US 8,592,406 B2
(45) Date of Patent: Nov. 26, 2013

(54) TRANSNASAL ANTICONVULSIVE PHARMACEUTICAL COMPOSITION COMPRISING POORLY SOLUBLE ANTICONVULSANT

(75) Inventors: Myoung-Ki Baek, Daejeon (KR); Jae-Hoon Jo, Daejeon (KR); Hye-Jin Chang, Daejeon (KR)

(73) Assignee: SK Biopharmaceuticals Co., Ltd., Seorin-dong, Jongro-gu, Seoul (KR)

( * ) Notice: Subject to any disclaimer, the term of this patent is extended or adjusted under 35 U.S.C. 154(b) by 27 days.

(21) Appl. No.: 12/940,563

(22) Filed: Nov. 5, 2010

(65) Prior Publication Data

US 2011/0172211 A1 Jul. 14, 2011
US 2012/0190670 A9 Jul. 26, 2012

Related U.S. Application Data

(63) Continuation of application No. PCT/KR2009/002567, filed on May 14, 2009.

(30) Foreign Application Priority Data

May 14, 2008 (KR) .................. 10-2008-0044481

(51) Int. Cl.
A61K 9/08 (2006.01)
(52) U.S. Cl.
USPC ........................................ 514/219; 514/218
(58) Field of Classification Search
None
See application file for complete search history.

(56) References Cited

U.S. PATENT DOCUMENTS

| | | | |
|---|---|---|---|
| 4,710,497 A | 12/1987 | Heller et al. | |
| 4,863,720 A | 9/1989 | Burghart et al. | |
| 4,950,664 A | 8/1990 | Goldberg | |
| 5,037,845 A | 8/1991 | Oxford | |
| 5,462,740 A | 10/1995 | Evenstad | |
| 5,466,699 A | 11/1995 | Robertson | |
| 6,627,211 B1 | 9/2003 | Choi et al. | |
| 6,750,237 B1 | 6/2004 | Dearn | |
| 7,745,430 B2 * | 6/2010 | Kim et al. ............... | 514/220 |
| 1,343,583 A1 * | 3/2012 | Bream et al. ............ | 514/221 |
| 2002/0032171 A1 | 3/2002 | Chen et al. | |
| 2002/0034539 A1 * | 3/2002 | Esposito et al. ........ | 424/451 |
| 2005/0002987 A1 * | 1/2005 | Choi et al. ............... | 424/434 |
| 2007/0021411 A1 | 1/2007 | Cloyd et al. | |
| 2007/0208011 A1 | 9/2007 | Cloyd et al. | |
| 2007/0225379 A1 * | 9/2007 | Carrara et al. ........... | 514/756 |
| 2008/0070904 A1 * | 3/2008 | Jamieson et al. ....... | 514/220 |
| 2008/0076761 A1 * | 3/2008 | Jamieson et al. ....... | 514/221 |
| 2008/0113970 A1 | 5/2008 | Kim | |
| 2008/0262445 A1 * | 10/2008 | Hsu et al. ............... | 604/307 |
| 2008/0279784 A1 * | 11/2008 | Cartt et al. .............. | 424/43 |
| 2009/0130216 A1 | 5/2009 | Cartt et al. | |
| 2009/0258865 A1 | 10/2009 | Cartt et al. | |

FOREIGN PATENT DOCUMENTS

| | | |
|---|---|---|
| EP | 386232 B1 | 8/1995 |
| EP | 532546 B1 | 3/1998 |
| WO | WO 90/02737 A1 | 3/1990 |
| WO | WO 90/07923 A1 | 7/1990 |
| WO | WO 01/01960 A1 | 1/2001 |
| WO | 0106987 | 2/2001 |
| WO | WO 2004/110403 A1 | 12/2004 |
| WO | WO 2009/027697 A2 | 3/2009 |
| WO | WO 2009/139589 A2 | 11/2009 |

OTHER PUBLICATIONS

The International Search Report and Written Opinion by the International Searching Authority, issued on Dec. 22, 2009, in the PCT application No. PCT/KR2009/002567.
Li et al., "Rapid-onset intranasal delivery of anticonvulsants: pharmacokinetic and pharmacodynamic evaluation in rabbits," Int. J. Pharm. Apr. 10, 2000;199(1):65-76.
Moolenaar et al., "Biopharmaceutics of rectal administration of drugs in man IX. Comparative biopharmaceutics of diazepam after single rectal, oral, intramuscular and intravenous administration in man," International Journal of Pharmaceutics vol. 5, Issue 2, Apr. 1980, pp. 127-137.
Lau et al., "Absorption of diazepam and lorazepam following intranasal administration," International Journal of Pharmaceutics vol. 54, Issue 2, Sep. 1, 1989, pp. 171-174.
Li et al., "Development of an ethyl laurate-based microemulsion for rapid-onset intranasal delivery of diazepam," Int. J. Pharm. Apr 26, 2002;237(1-2):77-85.

(Continued)

Primary Examiner — Shengjun Wang
Assistant Examiner — Svetlana M Ivanova
(74) Attorney, Agent, or Firm — Myers Bigel Sibley & Sajovec, P.A.

(57) ABSTRACT

There is provided a transnasal anticonvulsive pharmaceutical composition including a poorly soluble anticonvulsant. The anticonvulsive pharmaceutical composition comprising a poorly soluble anticonvulsant as an active component, which is transnasally spray-administered, comprises diethylene glycol monoethyl ether and fatty acid ester, wherein the fatty acid ester is selected from the group consisting of caprylocaproyl polyoxylglyceride, isopropyl palmitate, oleoyl polyoxylglyceride, sorbitan monolaurate 20, methyl laurate, ethyl laurate, and polysorbate 20. Also, the anticonvulsive pharmaceutical composition comprising a poorly soluble anticonvulsant as an active component, which is transnasally spray-administered, comprises diethylene glycol monoethyl ether, fatty acid ester, methylpyrrolidone, water and alcohol. Therefore, the transnasal anticonvulsive pharmaceutical composition may be useful to highly enhance the bioavailability of the poorly soluble anticonvulsant. Also, the transnasal anticonvulsive pharmaceutical composition may be useful to allow the poorly soluble anticonvulsant to show the improved viscosity and/or enhanced solubility in order to effectively deliver the poorly soluble anticonvulsant at a therapeutic dose.

15 Claims, 1 Drawing Sheet

(56) References Cited

OTHER PUBLICATIONS

Guo et al., "The effect of formulation variables and breathing patterns on the site of nasal deposition in an anatomically correct model," Pharmaceutical Research, vol. 22, No. 11, pp. 1871-1878.

Lindhardt et al., "Intranasal bioavailability of diazepam in sheep correlated to rabbit and man," Int. J. Pharm. 231:67-72 (2002).

International Search Report and Written Opinion Corresponding to International Application No. PCT/US2012/031453; Dated Sep. 26, 2012.

* cited by examiner (Primary spraying)  (Secondary spraying)

TRANSNASAL ANTICONVULSIVE PHARMACEUTICAL COMPOSITION COMPRISING POORLY SOLUBLE ANTICONVULSANT

CROSS-REFERENCE TO RELATED APPLICATIONS

This application claims priority from International Patent Application Serial No. PCT/KR2009/002567 filed May 14, 2009 which claims priority of Korean Patent Application No.: 10-2008-0044481 filed May 14, 2008.

BACKGROUND OF THE INVENTION

1. Field of the Invention

The present invention relates to a transnasal anticonvulsive pharmaceutical composition comprising a poorly soluble anticonvulsant, and more particularly, to a transnasal anticonvulsive pharmaceutical composition having enhanced bioavailability to be effectively delivered at a therapeutic dose, and improved viscosity and/or enhanced solubility to show desirable properties such as spray angle and spraying shape.

2. Description of the Prior Art

Status epilepticus is a neurologically emergent condition, leading to 3-35% mortality. The chief target for treatment of status epilepticus is to swiftly manage pathological attacks. However, when the symptoms of status epilepticus last for a long time without swift management, it is difficult to control the status epilepticus, and the risk of permanent brain damage increases. Therefore, it is very important to swiftly treat patients by administering an adequate dose of a pharmaceutical composition having an adequate pharmaceutical formulation containing an effective drug.

Recently, it has been known that a variety of pharmacotherapies are used to treat status epilepticus. Diazepam and lorazepam are benzodiazepine drugs that have been most widely used for this purpose. Also, the intravenous administration of an anticonvulsant is the swiftest way to suppress epileptic convulsions. However, when the intravenous administration is not easy, for example, when the intravenous administration is delayed due to technical difficulties, such as the lack of a sterilizer and a skilled practitioner, and when there is phlebitis to possibly develop, it may be more desirable to administer an anticonvulsant via other routes. Also, intravenous drugs are often associated with hypotension, cardiac dysrhythmia or central nervous system degeneracy. In this regard, Moolenar, et al. made an attempt to administer diazepam to human beings via various routes such as intramuscular injection, oral tablet and rectal solution (Int. J. Pharm., 5: 127-137 (1986)), but they found that the rectal administration of the diazepam provides its highly swift absorption. Therefore, it may be considered that rectal administration be used as an alternative to an intravenous injection. Kenneth L., et al. has developed the rectal formulation (U.S. Pat. No. 5,462,740) as a useful method. This rectal route of administration is a very uncomfortable route used for the emergency treatment and the drug administration to patients with age over the adolescent period.

Nasal mucosae provide a virtual route for therapeutic effects of many medicinal substances. Nasal administration has an advantage in that drugs may be easily and simply administered to achieve systemic or topical effects, when necessary. In particular, zolmitriptan (U.S. Pat. No. 5,466, 699), which had been developed as one of drugs for the central nervous system to treat migraine, was developed and commercially available as a nasal spray formulation (U.S. Pat. No. 6,750,237), and sumatriptan (U.S. Pat. No. 5,037, 845) was also developed and commercially available as a nasal spray. However, unlike thse two water-soluble drugs, most drugs hardly have solubility corresponding to a desired therapeutic dose, and one leading problem associated with the nasal administration of drugs may not be solved by the simple transnasal administration means since most of the drug molecules are not easily or are slowly spread through the nasal mucosae. An additional restriction on the nasal administration of drugs is that the drugs are restrictedly administered in a small dose. In general, it is impossible to administer drugs in a dose of approximately 150 ul or more per nostril, and an amount of a mixture exceeding the dose range of the drugs are extruded into the pharynx, and swallowed.

Also, the drugs such as diazepam and lorazepam are difficult to be developed into a formulation suitable for nasal spray administration since they have low solubility in water that is widely used to dissolve drugs. Therefore, the development of solvents for nasal spray administration, which dissolve a desired drug, for example, diazepam and lorazepam, in a high concentration and give no stimulus to the nasal mucosae, is highly required.

The nasal absorption of drugs may be augmented by administering the drugs and a chemical aid or a penetration enhancer at the same time. For example, Lau and Slattery [Lau, et al., Int. J. Pharm., 54: 171-174 (1989)] made an attempt to dissolve a benzodiazepine (i.e. diazepam) in various solvents (for example, triacetin, dimethyl sulfoxide, PEG 400, Cremophor EL, Lipal-9-LA, diisopropyl adipate and azone) and administer the dissolved drug.

However, the diazepam was dissolved in most of the solvents within a desired concentration, but the desired concentration of the solvents is too pungent to be used for transnasal administration. Cremophor EL has been known to have the lowest stimulus to the nasal mucosal tissue, but its nasal absorption is rather slow ($T_{max}$: 1.4 hours) in humans in use of these vehicles, and the peak concentration is lower than that observed after the intravenous administration. Recently, Li, et al. (International Journal of Pharmaceutics Vol. 237, pp 77-85, 2002) proposed a microemulsion for rapid-onset transnasal delivery of diazepam.

Also, U.S. Pat. No. 6,627,211 B1 (KR 2002-0059583) discloses transnasal anticonvulsive compositions comprising diazepam. Here, the diazepam is dissolved in a soluble formulation such as aliphatic alcohol, a polar solvent (i.e. glycol), water, etc. Also, published US patent application No. 2005-0002987 A1 (KR 2006-0012030) discloses microemulsions containing diazepam used for transnasal administration. Here, the diazepam is dissolved in a vehicle comprising equivalent amounts of fatty acid ester and water and the balance of hydrophilic surfactant, polar solvent (i.e. glycol), etc.

When drugs are nasally administered to patients, their fine and uniform dispersion is important. A spraying shape test used to evaluate the efficiency of a nasal spraying agent has been widely used to evaluate a nasal administration formulation in vitro. This spraying shape test is important since the in vivo delivery of a drug is possible when the drug uniformly distributed following its nasal spraying. For example, USA test standards on the spraying shape test has been set, and must be reproducible and be suitable for these test standards in order to deliver a suitable drug to treat its corresponding disease (U.S. Food and Drug Administration's (FDA) Draft Guidance for Industry: Bioavailability and Bioequivalence Studies for Nasal Aerosols and Nasal Spray for Local Action (June 1999).

According to the report by Yang, et al. (Pharmaceutical Research Vol 22, No. 11, pp. 1871-1878, 2005), a formulation having a small droplet size and low viscosity is delivered to central and inner regions of the nasal cavities, which indicates that the formulation is more desirably distributed nasally than formations having a big droplet size and high viscosity. Therefore, it is important that the nasal formulation has a viscosity and droplet size suitable for the purpose of drug delivery. There is a significant need for a pharmaceutical composition having physical properties suitable for transnasal administration, such as enhanced bioavailability of a poorly soluble anticonvulsant, viscosity and/or solubility, etc.

Such compositions are provided in accordance with the present invention. Further, the present invention provides a method for treating convulsions including: administering to patients suffering from the convulsions a sufficient amount of a pharmaceutical composition to treat the convulsions.

SUMMARY OF THE INVENTION

According to an aspect of the present invention, there is provided an anticonvulsive pharmaceutical composition comprising a poorly soluble anticonvulsant as an active component, which is transnasally spray-administered, the anticonvulsive pharmaceutical composition including diethylene glycol monoethyl ether and fatty acid ester, wherein the fatty acid ester is selected from the group consisting of caprylocaproyl polyoxylglyceride, isopropyl palmitate, oleoyl polyoxylglyceride, sorbitan monolaurate 20, methyl laurate, ethyl laurate, and polysorbate 20.

According to another aspect of the present invention, there is provided an anticonvulsive pharmaceutical composition comprising a poorly soluble anticonvulsant as an active component, which is transnasally spray-administered, the anticonvulsive pharmaceutical composition including diethylene glycol monoethyl ether, fatty acid ester, methylpyrrolidone, water and alcohol.

According to still another aspect of the present invention, there is provided a method for treating convulsions, the method including: transnasally spray-administering to patients suffering from the convulsions a sufficient amount of the pharmaceutical composition to treat the convulsions.

BRIEF DESCRIPTION OF THE DRAWINGS

The present invention will be more clearly understood from the following detailed description taken in conjunction with the accompanying drawings, in which.

DESCRIPTION OF THE PREFERRED EMBODIMENTS

Figure 1:
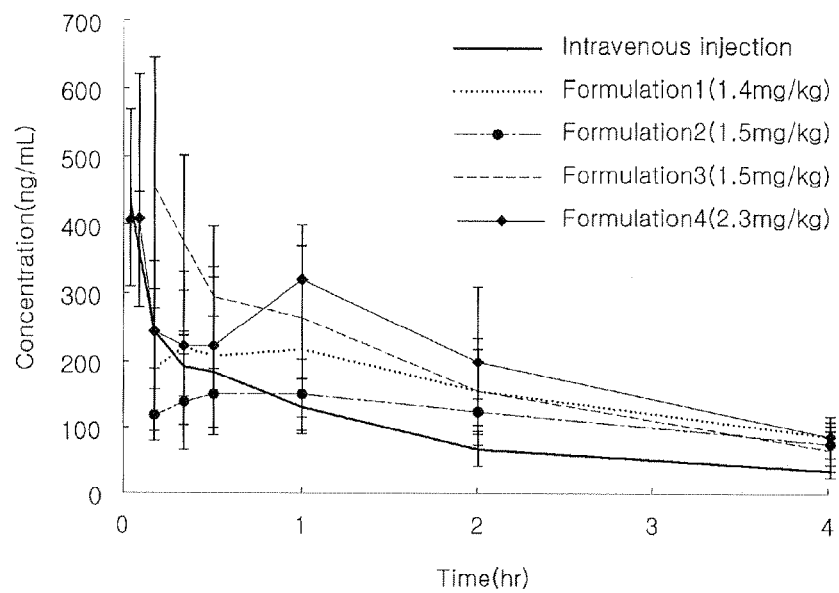
FIG. 1 shows a pharmacokinetic profile after intravenous (i.v) and transnasal administration of formulations containing diazepam as an anticonvulsant according to one exemplary embodiment of the present invention.

Hereinafter, exemplary embodiments of the present invention will be described in detail.

The present inventors have found that, when an anticonvulsive pharmaceutical composition containing a poorly soluble anticonvulsant as an active component, which is used for transnasal administration, include diethylene glycol monoethyl ether and certain fatty acid ester in the use of a minimum content of water and ethanol or without use of the water and ethanol, the solubility of diazepam in the anticonvulsive pharmaceutical composition is enhanced by up to 15.39%, compared to 2.5% as in U.S. Pat. Nos. 6,627,211 and 4.1% as in US Patent Application No. 2005-0002987, and the bioavailability of the diazepam is enhanced by up to 119%, compared to 65% as in both the above patent publications. Also, they have found that lorazepam widely used in clinical use is also nasally delivered to show 35% bioavailability. Therefore, the present invention was completed on the basis of the above facts.

The present invention provides an anticonvulsive pharmaceutical composition, which is nasally sprayed for the purpose of transnasal administration, contains as an active component a poorly soluble anticonvulsant selected from the group consisting of diazepam and lorazepam, and further include diethylene glycol monoethyl ether and fatty acid ester, wherein the fatty acid ester is selected from the group consisting of caprylocaproyl polyoxylglyceride, isopropyl palmitate, oleoyl polyoxylglyceride, sorbitan monolaurate 20, methyl laurate, ethyl laurate, and polysorbate 20.

According to the present invention, the diazepam or lorazepam used as the active component is preferably present in a content of 1 to 20% by weight, based on the total weight of the pharmaceutical composition, but the present invention is not particularly limited thereto.

The diethylene glycol monoethyl ether used in the present invention is preferably present in a content of 45 to 60% by weight, based on the total weight of the pharmaceutical composition. For example, Transcutol P (commercially available from Gattefosse) may be used as the diethylene glycol monoethyl ether.

The fatty acid ester used in the present invention includes caprylocaproyl polyoxylglyceride, isopropyl palmitate, oleoyl polyoxylglyceride, sorbitan monolaurate 20, methyl laurate, ethyl laurate, and polysorbate 20, and they may be used alone or in combinations thereof. In this case, the fatty acid ester is preferably present in a content of at least 30% by weight or more, based on the total weight of the pharmaceutical composition. More preferably, the fatty acid ester is present in a content of 30 to 50% by weight, based on the total weight of the pharmaceutical composition.

According to one exemplary embodiment of the present invention, the pharmaceutical composition of the present invention includes 5 to 15% by weight of at least one poorly soluble anticonvulsant selected from the group consisting of diazepam and lorazepam, 45 to 60% by weight of diethylene glycol monoethyl ether, and 35 to 50% by weight of fatty acid ester, wherein the fatty acid ester includes at least one selected from the group consisting of caprylocaproyl polyoxylglyceride, isopropyl palmitate, oleoyl polyoxylglyceride, sorbitan monolaurate 20, methyl laurate, ethyl laurate, and polysorbate 20. More preferably, at least one selected from the group consisting of caprylocaproyl polyoxylglyceride, isopropyl palmitate, oleoyl polyoxylglyceride, sorbitan monolaurate 20, and polysorbate 20 may be used as the fatty acid ester.

Also, according to another exemplary embodiment of the present invention, there is provided an anticonvulsive pharmaceutical composition, which is transnasally spray-administered, containing as an active component at least one poorly soluble anticonvulsant selected from the group consisting of diazepam and lorazepam, the anticonvulsive pharmaceutical composition including diethylene glycol monoethyl ether, fatty acid ester, methylpyrrolidone, water and alcohol.

According to this exemplary embodiment of the present invention, the diazepam or lorazepam is preferably present in a content of 1 to 20% by weight, based on the total weight of the pharmaceutical composition, but the present invention is not particularly limited thereto. Also, the diethylene glycol monoethyl ether is preferably present in a content of 45 to 60% by weight, based on the total weight of the pharmaceutical composition. For example, Transcutol P (commercially available from Gattefosse) may be used as the diethylene glycol monoethyl ether.

The fatty acid ester used according to this exemplary embodiment of the present invention includes, but is not particularly limited to, caprylocaproyl polyoxylglyceride, isopropyl palmitate, oleoyl polyoxylglyceride, sorbitan monolaurate 20, methyl laurate, ethyl laurate, polysorbate 20 and propylene glycol monocaprylate, and they may be used alone or in combinations thereof. Therefore, the fatty acid ester is preferably present in a content of at least 30% by weight or more, based on the total weight of the pharmaceutical composition. More preferably, the fatty acid ester is present in a content of 30 to 50% by weight, based on the total weight of the pharmaceutical composition.

More preferably, methyl laurate is used as the fatty acid ester, and is present in a content of at least 30% by weight or more, based on the total weight of the pharmaceutical composition. More preferably, the fatty acid ester is present in a content of 30 to 50% by weight, based on the total weight of the pharmaceutical composition.

In addition, propylene glycol monocaprylate is preferably used as the fatty acid ester. In this case, the propylene glycol monocaprylate is preferably present in a content of 5 to 25% by weight, based on the total weight of the pharmaceutical composition, but the present invention is not particularly limited thereto.

Additionally, the alcohol used according to this exemplary embodiment of the present invention preferably includes, but is not particularly limited to, ethanol.

Also, according to one exemplary embodiment of the present invention, the pharmaceutical composition of the present invention contains 5 to 15% by weight of at least one poorly soluble anticonvulsant selected from the group consisting of diazepam and lorazepam, and also 40 to 60% by weight of diethylene glycol monoethyl ether, 5 to 15% by weight of methyl laurate, 5 to 30% by weight of methylpyrrolidone, 1 to 5% by weight of water and 5 to 10% by weight of ethanol.

Also, the pharmaceutical composition according to one exemplary embodiment of the present invention may further include dimethyl isosorbide. In this case, the dimethyl isosorbide is preferably present in a content of 5 to 10% by weight, based on the total weight of the pharmaceutical composition, but the present invention is not particularly limited thereof.

The pharmaceutical composition according to one exemplary embodiment of the present invention preferably has a fluid kinematic viscosity of 10 Me/sec or less so that it can be transnasally spray-administered. Therefore, the pharmaceutical composition according to one exemplary embodiment of the present invention is easy to be nasally administered. The nasal administration is characterized in that this method is highly simple, compared to other methods of parenteral administrations, and such low viscosity allow a drug to be effectively delivered in a desired therapeutic dose by using a commercially available nasal spray. A pharmaceutical composition having a poorly insoluble drug dissolved therein may not be delivered using a conventional nasal spray since the pharmaceutical composition has a high viscosity, and therefore it is necessary to use a nasal spray for high-viscosity compositions or an available high-pressure pump. In this regard, the pharmaceutical composition according to one exemplary embodiment of the present invention may be constantly absorbed and stably administered using a conventional nasal spray system such as uni-dose, bi-dose and multi-dose spray devices (commercially available from Pfeiffer), and Acuspray spray (BD).

According to another exemplary embodiment of the present invention, there is provided a method for treating convulsions including: transnasally spray-administering to patients suffering from the convulsions a sufficient amount of the pharmaceutical composition to treat the convulsions.

The pharmaceutical composition according to one exemplary embodiment of the present invention has an advantage in that the solubility of diazepam in the anticonvulsive pharmaceutical composition is enhanced by up to 15.39%, compared to 2.5% as in U.S. Pat. Nos. 6,627,211 and 4.1% as in US Patent Application No. 2005-0002987, and the bioavailability of the diazepam is enhanced by up to 119%, compared to 65% as in both the above patent publications, as corroborated in Examples described later. Also, the pharmaceutical composition has an advantage in that lorazepam widely used in clinical tests also shows 35% bioavailability, which indicates that the bioavailability of the poorly soluble anticonvulsant is highly enhanced. Therefore, the transnasal anticonvulsive pharmaceutical composition according to one exemplary embodiment of the present invention is made very easy to be administered. When compared to the parenteral administration, for example, a simple spray, a dropper, or a nebulizer may be especially used to satisfy the requirements regarding the rapid and convenient delivery of drugs for emergency treatment of an acute convulsive attack of epilepsy. In the clinical term, the transnasal administration often makes, it possible to enhance the duration of anticonvulsive activity. A therapeutic dose of the transnasal anticonvulsive pharmaceutical composition may be more effectively and exactly controlled by administering the formulation of the present invention once or several times. Although the anticonvulsant is described as a model compound in the present invention, the present invention is applicable to other biological activators that may be used for mucosal administration to humans and animals. Hence, the transnasal anticonvulsive pharmaceutical composition according to one exemplary embodiment of the present invention may be useful to highly enhance the bioavailability of the poorly soluble anticonvulsant. Further, the transnasal anticonvulsive pharmaceutical composition according to one exemplary embodiment of the present invention may be useful to allow the poorly soluble anticonvulsant to show the improved viscosity and/or enhanced solubility in order to effectively deliver the poorly soluble anticonvulsant at a therapeutic dose.

EXAMPLES

Now, the present invention will be described in more detail with reference to the following examples. These examples are provided only for illustrating the present invention and should not be construed as limiting the scope and spirit of the present invention in any manner.

Example 1

Preparation of Solution for Transnasal Administration

Diethylene glycol monoethyl ether and fatty acid ester were put into a paddle-type stirrer, and completely mixed.

Then, a hydrophobic solvent, water and ethanol were sequentially added, and mixed with the resulting mixture, when necessary. Here, the expression "complete mixing" means a state where the mixture solution is clear and transparent without any of phase separation and turbidity.

Example 2

Solubility Test of Diazepam 100 mg of diazepam was added to 500 μl of the mixture prepared in the method of Example 1 so that each formulation can have its composition ratio as listed in the following Tables. Then, the resulting mixture was stirred at a room temperature for 24 hours, and then filtered through a 0.45-micrometer membrane filter. Then, the resulting filtrate was subject to liquid high performance liquid chromatography to analyze a concentration of diazepam. A column used in this experiment was a 10 mm C18 column with 30 cm×3.9 mm, and a mobile phase was a mixture (by volume ratio) composed of 65% of methanol and 35% distilled water. A flow rate was set to 1.4 mL/min, and the detection was performed at a wavelength of 254 nm. p-Hydroxyanisole was used as an analytical internal standard substance. The results are listed in the following Tables 1 to 8. In the final solution in which diazepam is dissolved, each component is represented by a final composition ratio (% by weight).

TABLE 1

(Formulation 1)

| Components | Final composition ratio (% by weight) |
|---|---|
| Diethylene glycol monoethyl ether | 48.3% |
| Caprylocaproyl polyoxylglyceride | 24.3% |
| Oleoyl polyoxylglyceride | 7.3% |
| Sorbitan monolaurate 20 | 10.9% |
| Diazepam | 9.13% |

TABLE 2

(Formulation 2)

| Components | Final composition ratio (% by weight) |
|---|---|
| Diethylene glycol monoethyl ether | 48.64% |
| Caprylocaproyl polyoxylglyceride | 24.36% |
| Isopropyl palmitate | 7.30% |
| Sorbitan monolaurate 20 | 10.95% |
| Diazepam | 8.75% |

TABLE 3

(Formulation 3)

| Components | Final composition ratio (% by weight) |
|---|---|
| Diethylene glycol monoethyl ether | 48.54% |
| Caprylocaproyl polyoxylglyceride | 24.32% |
| Isopropyl palmitate | 7.29% |
| Polysorbate 20 | 10.93% |
| Diazepam | 8.92% |

TABLE 4

(Formulation 4)

| Components | Final composition ratio (% by weight) |
|---|---|
| Diethylene glycol monoethyl ether | 45.38% |
| Caprylocaproyl polyoxylglyceride | 15.13% |
| Sorbitan monolaurate 20 | 16.76% |
| Isopropyl palmitate | 11.17% |
| Distilled water | 4.65% |
| Diazepam | 6.91% |

TABLE 5

(Formulation 5)

| Components | Final composition ratio (% by weight) |
|---|---|
| Diethylene glycol monoethyl ether | 56.64% |
| Sorbitan monolaurate 20 | 8.50% |
| Oleoyl polyoxylglyceride | 5.66% |
| Methylpyrrolidone | 17.70% |
| Diazepam | 11.5% |

TABLE 6

(Formulation 6)

| Components | Final composition ratio (% by weight) |
|---|---|
| Diethylene glycol monoethyl ether | 42.61% |
| Propylene glycol monocaprylate | 21.30% |
| Methyl laurate | 10.75% |
| Dimethyl isosorbide | 7.10% |
| Methylpyrrolidone | 7.10% |
| Diazepam | 11.23% |

TABLE 7

(Formulation 7)

| Components | Final composition ratio (% by weight) |
|---|---|
| Diethylene glycol monoethyl ether | 41.56% |
| Methyl laurate | 8.66% |
| Propylene glycol monocaprylate | 6.93% |
| Methylpyrrolidone | 20.78% |
| Distilled water | 1.73% |
| Ethanol | 6.93% |
| Diazepam | 13.41% |

TABLE 8

(Formulation 8)

| Components | Final composition ratio (% by weight) |
|---|---|
| Diethylene glycol monoethyl ether | 40.61% |
| Methyl laurate | 8.46% |
| Methylpyrrolidone | 27.08% |
| Distilled water | 1.69% |
| Ethanol | 6.77% |
| Diazepam | 15.39% |

Example 3

Viscosity Measurement

A capillary viscometer (Cannon-Fenske-Routine viscometer) was used as the viscometer, and the viscosity was measured at a constant temperature of 40□ in a water bath by using the viscometer attached to a fixing apparatus. A suction tube was used to transfer the mixture prepared in Example 2 according to the method of Example 1 to a starting line of the viscometer. Then, the mixture was kept for approximately 10 min so that it can drop along a capillary tube, and the time required for the dropping of the mixture was measured. The kinematic viscosity was calculated as represented by the following Equation 1. Here, a viscosity unit was represented by $mm^2$/sec.

$$\text{Kinematic viscosity}(v) = \text{Viscometer constant} (K=0.01547\ mm^2/s^2) \times \text{elution time}(t) \quad \text{Equation 1}$$

TABLE 9

Viscosity measurement results

| Formulations | mm2/sec |
|---|---|
| Formulation 1 | 17.1 |
| Formulation 2 | 14.5 |
| Formulation 3 | 17.7 |
| Formulation 4 | 15.5 |
| Formulation 5 | 8.5 |
| Formulation 6 | 2.93 |
| Formulation 7 | 2.23 |
| Formulation 8 | 1.97 |

Example 4

Evaluation of Spray Pattern

Figure 3:
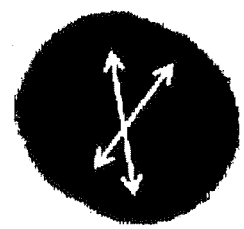
FIG. 3 shows a spray pattern obtained by spraying a formulation according to one exemplary embodiment of the present invention using a nasal spray.
Figure 3:
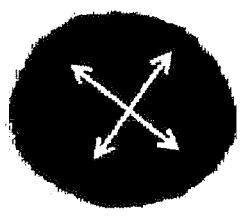

A trace of an edible blue pigment was mixed with the mixture of the prepared formulation 2, and the resulting mixture was loaded into a nasal spray (a bi-dose system, Pfeiffer), and then sprayed twice on a white filer positioned 3 centimeters from the nasal spray, thus to analyze a spray pattern. The results are shown in FIG. 3 (Left—Primary spraying, Right—Secondary spraying).

The spray pattern was oval, which is close to round, and the ovality ratios were 1.25 in the primary spraying (Left photograph of FIGS. 3) and 1.0 in the secondary spraying (Right photograph of FIG. 3), as represented by a ratio of maximum diameter ($D_{max}$) to minimum diameter ($D_{min}$) of the oval spray pattern. US Food and Drug Administration (FDA) regulations for inhaled and nasal drug products (Guidance for industry, Nasal spray and inhalation solution, suspension and spray drug products, chemistry, manufacturing, and controls documentation, 2002) recommends an ovality ratio of 1.0 to 1.3. Therefore, it was confirmed that the transnasal anticonvulsive pharmaceutical composition according to one exemplary embodiment of the present invention shows desirable spray angle and spraying shape so that it can be effectively delivered at a therapeutic dose.

Example 5

Pharmacokinetic Test of Diazepam-Containing Nasal Formulation in Rabbit (Bioavailability Test)

Right before this experiment, rabbits (n=3) were weighed, and a mixed solution including 25 mg of ketamine and 4 mg of xylazine was intramuscularly injected to the rabbits per kilogram (Kg) in order to anesthetize the rabbits, and a catheter was fastened to each rabbit to collect blood from rabbits' otic artery. An intravenous injection was performed by administering the mixed solution to the rabbits via the rabbits' otic artery at a dose of 1 mg/kg for approximately 20 seconds. A Melode injection (diazepam, 10 mg/2 mL; Dong Wha Pharm. Ind. Co. Ltd.) was used as intravenous injection. In order to transnasally administer each of the formulations 1, 2, 3 and 7 prepared in Example 2 to one nostril of each rabbit, a concentration of diazepam in the formulations 1, 2 and 3 was set to 8%, and its dosage was set to 1.4 mg/kg. Also, a concentration of diazepam in the formulation 4 was set to 10%, and its dosage was set to 2.3 mg/kg. Then, each formulation was sprayed to the rabbits using a Pfeiffer nasal spry system. For the formulations prepared in Example 2, 8% diazepam is dissolved in the case of the formulations 2 and 3, and 10% diazepam is dissolved in the case of the formulation 4.

Blood samples (1 Ml) were collected from the rabbits' otic artery at 0, 2, 5, 10, 20, 30, 45, 60 and 120 minutes after the intravenous injection and transnasal administration of each formulation. Each of the blood samples was centrifuged to separate rabbit plasma, which was stored at −20° C. until is will be used for analysis. In order to analyze the plasma samples, each of the plasma samples (0.5 Ml) was exactly transferred to a 1.5 Ml polypropylene centrifuge tube. The mixture was vortexed for 30 seconds, and centrifuged at a rotary speed of 400 rpm for 10 minutes. A concentration of the diazepam in the plasma sample was analyzed using LC-MS/MS. A 0.1% formic acid-acetonitrile/deionized water (60/40, v/v) mixed solution was used as a mobile phase, a flow rate was set to 0.25 mL/min, and Xterra®MS $C_{18}$ (3.0×50 mm, 2.5 micrometers, Waters, USA) was used as a column. The peak detection was performed by a multiple reaction monitoring (MRM) method using a triple-quadrupole mass spectrometry. The ionization was analyzed in a positive mode using an electrospray ionization (ESI) method, and the ion spray temperature was set to 500□. Protonated molecular ions of the diazepam and the internal standard substance were monitored at m/z 284.9 and 268.0, respectively, using an MRM method, and their product ions were monitored at m/z 154.1 and 155.0, respectively. An area under the plasma concentration-time curve (AUC) from 0 to 4 hours was calculated according to the linear trapezoidal method. The results are listed in the following Table 10 and are shown in FIG. 1.

TABLE 10 bioavailability of diazepam-containing transnasal administration formulations

| | Bioavailability (F, %) |
|---|---|
| Intravenous injectable formulation | 100% |
| Formulation 1 | 109% |
| Formulation 2 | 82% |
| Formulation 3 | 119% |
| Formulation 4 | 85% |

Example 6

Pharmacokinetic Test of Lorazepam-Containing Nasal Formulation in Rabbit (Bioavailability Test)

Figure 2:
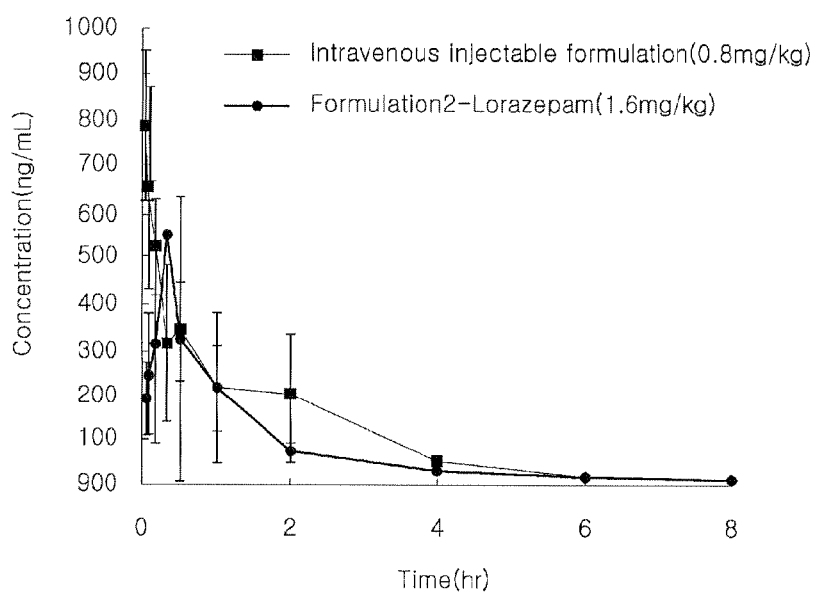
FIG. 2 shows a pharmacokinetic profile after intravenous (i.v) and transnasal administration of formulations containing lorazepam as an anticonvulsant according to one exemplary embodiment of the present invention.

Lorazepam was dissolved instead of the diazepam in a solution of formulation 1 so that the lorazepam was present in a content of 9%. Then, this experiment was performed in the same manner as in Example 5. In this case, the lorazepam was set to a concentration of 9%, and was administered at a dose of 1.6 mg/kg. Ativan injection (4 mg/mL, Il Dong Pharm, Co., Ltd) was used as the lorazepam in the intravenous injectable formulation, and was administered at a dose of 0.8 mg/kg. Each plasma sample pre-treated with acetonitrile was quantified under the following LC/MS/MS conditions. A 0.1% formic acid-acetonitrile/deionized water (60/40, v/v) mixed solution was used as a mobile phase, a flow rate was set to 0.25 mL/min, and Xterra®NS $C_{18}$ (3.0×50 mm, 2.5 micrometers, Waters, USA) was used as a column. The peak detection was performed by a multiple reaction monitoring (MRM) method using a triple-quadrupole mass spectrometry. The ionization was analyzed in a positive mode using an electrospray ionization (ESI) method, and the ion spray temperature was set to 500° C. Protonated molecular ions of the diazepam and the internal standard substance were monitored at m/z 320.9 and 268.0, respectively, using an MRM method, and their product ions were monitored at m/z 275.0 and 155.0, respectively. The results are listed in the following Table 11 and are shown in FIG. 2.

TABLE 11 bioavailability of lorazepam-containing transnasal administration formulations

| | Bioavailability (F, %) |
|---|---|
| Intravenous injectable formulation | 100% |
| Formulation 1-Lorazepam | 33% |

What is claimed is:

1. An anticonvulsive pharmaceutical composition for transnasal administration, consisting essentially of:
    about 1% to about 20% by weight of a poorly soluble anticonvulsant,
    about 40% to about 60% by weight of diethylene glycol monoethyl ether,
    about 5% to about 30% by weight of methylpyrrolidone,
    about 1% to about 5% by weight of water,
    about 5% to about 10% by weight of alcohol, and
    fatty acid ester which is methyl laurate at about 5% to about 15% by weight of the pharmaceutical composition and/or propylene glycol monocaprylate at about 5% to about 25% by weight of the pharmaceutical composition.

2. The anticonvulsive pharmaceutical composition of claim 1, wherein the poorly soluble anticonvulsant is diazepam or lorazepam.

3. The anticonvulsive pharmaceutical composition of claim 1, wherein the poorly soluble anticonvulsant is diazepam.

4. The anticonvulsive pharmaceutical composition of claim 1, wherein the alcohol is ethanol.

5. The anticonvulsive pharmaceutical composition of claim 1, wherein the pharmaceutical composition has a kinematic viscosity of 10 $mm^2$/sec or less for transnasal spray-administration.

6. The anticonvulsive pharmaceutical composition of claim 1, wherein the fatty acid ester is methyl laurate at about 5% to about 15% by weight of the pharmaceutical composition and propylene glycol monocaprylate at about 5% to about 25% by weight of the pharmaceutical composition.

7. A method for treating a convulsion in a subject, comprising:
    transnasally administering to the subject in need of such treatment a therapeutically effective amount of the pharmaceutical composition of claim 1.

8. The method of claim 7, wherein the transnasally administering comprises transnasally spraying the pharmaceutical composition.

9. The anticonvulsive pharmaceutical composition of claim 1, wherein the poorly soluble anticonvulsant is diazepam at about 5% to about 15% by weight.

10. An anticonvulsive pharmaceutical composition for transnasal administration, consisting essentially of:
    about 1% to about 20% by weight of diazepam,
    about 40% to about 60% by weight of diethylene glycol monoethyl ether,
    about 5% to about 30% by weight of methylpyrrolidone,
    about 1% to about 5% by weight of water,
    about 5% to about 10% by weight of ethanol,
    about 5% to about 15% by weight of methyl laurate, and
    about 5% to about 25% by weight of propylene glycol monocaprylate.

11. A method for treating a convulsion in a subject, comprising:
    transnasally administering to the subject in need of such treatment a therapeutically effective amount of the pharmaceutical composition of claim 10.

12. The method of claim 11, wherein the transnasally administering comprises transnasally spraying the pharmaceutical composition.

13. An anticonvulsive pharmaceutical composition for transnasal administration, consisting essentially of:
    about 5% to about 15% by weight of diazepam,
    about 40% to about 60% by weight of diethylene glycol monoethyl ether,
    about 5% to about 30% by weight of methylpyrrolidone,
    about 1% to about 5% by weight of water,
    about 5% to about 10% by weight of ethanol,
    about 5% to about 15% by weight of methyl laurate, and
    about 5% to about 25% by weight of propylene glycol monocaprylate.

14. A method for treating a convulsion in a subject, comprising:
    transnasally administering to the subject in need of such treatment a therapeutically effective amount of the pharmaceutical composition of claim 13.

15. The method of claim 14, wherein the transnasally administering comprises transnasally spraying the pharmaceutical composition.

* * * * *

UNITED STATES PATENT AND TRADEMARK OFFICE
CERTIFICATE OF CORRECTION

PATENT NO. : 8,592,406 B2  
APPLICATION NO. : 12/940563  
DATED : November 26, 2013  
INVENTOR(S) : Baek et al.

Page 1 of 1

It is certified that error appears in the above-identified patent and that said Letters Patent is hereby corrected as shown below:

On Title Page:  
Item (56), References Cited, U.S. Patent Documents, Page 1:  
  Please correct: "1,343,583 03/2012 Bream et al. 514/221"  
      to read -- 13/435,837 03/2012 Bream et al. 514/221 --

In the Specification:  
Column 11, Line 11, Title: Please correct "and Xterra®NS $C_{18}$"  
           to read -- and Xterra® MS $C_{18}$ --

Signed and Sealed this  
Third Day of June, 2014

Michelle K. Lee  
*Deputy Director of the United States Patent and Trademark Office*